United States Patent [19]

Motoyama et al.

[11] Patent Number: 5,985,172
[45] Date of Patent: Nov. 16, 1999

[54] RACEMIC COMPOUND AND ANTI-FERROELECTRIC LIQUID CRYSTAL COMPOSITION CONTAINING THE COMPOUND

[75] Inventors: Yuki Motoyama; Hiroshi Mineta; Tomoyuki Yui; Masahiro Johno, all of Tsukuba, Japan

[73] Assignee: Mitsubishi Gas Chemical Company, Inc., Tokyo, Japan

[21] Appl. No.: 08/975,245

[22] Filed: Nov. 21, 1997

[30] Foreign Application Priority Data

Nov. 22, 1996 [JP] Japan .................................. 8-312012

[51] Int. Cl.$^6$ .......................... C09K 19/20; C09K 19/12
[52] U.S. Cl. .............................. 252/299.64; 252/299.64; 252/299.65; 252/299.66
[58] Field of Search ........................ 252/299.01, 299.67, 252/299.64, 299.65, 299.66; 349/174

[56] References Cited

U.S. PATENT DOCUMENTS 5,840,209  11/1998  Mineta et al. ...................... 252/299.67

FOREIGN PATENT DOCUMENTS

| 0341686 | 11/1989 | European Pat. Off. . |
| 0347940 | 12/1989 | European Pat. Off. . |
| 0517504 | 12/1992 | European Pat. Off. . |
| 0562627 | 9/1993  | European Pat. Off. . |
| 0582468 | 2/1994  | European Pat. Off. . |
| 0807675 | 11/1997 | European Pat. Off. . |

OTHER PUBLICATIONS

Neubert, et al., "Synthesis and Mesomorphic Properties of Some Aromatic Esters Containing 2–Butyl, 2–Octyl and 2–Methylbutyl Moieties in the Terminal Chains", Mol. Cryst. Liq. Cryst., 1993, vol. 237, pp. 193–205.

A.D.L. Chandani, et al., "Tristable Switching in Surface Stabilized Ferroelectric Liquid Crystals with a Large Spontaneous Polarization", Japan Journal of Appl. Physics, 27(5), L729–L732 (May 1988).

A.D.L Chandani, et al., "Novel Phases Exhibiting Tristable Switching", Japan Journal of Appl. Physics, 28(7), L1261–L1264 (Jul. 1989).

A.D.L. Chandani, et al., "Antiferroelectric Chiral Smectic Phases Responsible for the Tristable Switching in MHPOBC", Japan Journal of Appl. Physics, 28(7), L1265–L1268 (Jul. 1989).

M. Johno, et al., "Smectic Layer Switching by an Electric Field in Ferroelectric Liquid Crystal Cells", Jap. Jour. Appl. Phys. 28(1), L119–L120 (Jan. 1989).

M. Johno et al., Correspondence between Smectic Layer Switching and DC Hysteresis of Apparent Tilt Angle in an Antiferroelectric Liquid Crystal Mixture, Jap. Jour. Appl. Phys., 29(1), L111–L114 (Jan. 1990).

N. Yamamoto, et al., Full–Color Antiferroelectric Liquid Crystal Display, Preprints—Fourth International Conference on Ferroelectric Liquid Crystals, Tokyo, Japan, pp. 77–78 (1993).

*Primary Examiner*—Shean C. Wu
*Attorney, Agent, or Firm*—Sherman and Shalloway

[57] ABSTRACT

A racemic compound of the formula (1)

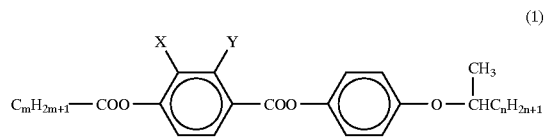

and an anti-ferroelectric liquid crystal composition consisting essentially of said racemic compound and one anti-ferroelectric liquid crystal compound of the formula (2) or a mixture of two or more compounds selected from anti-ferroelectric liquid crystal compounds of the formula (2),

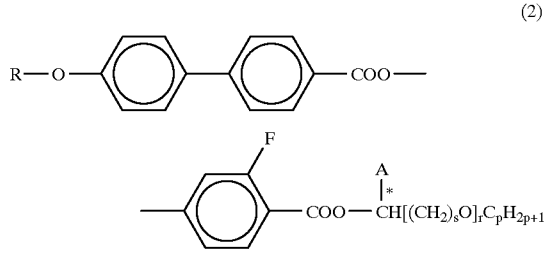

said composition having excellent steepness of threshold, having an anti-ferroelectric phase over a broad temperature range and having the performance of a high response speed and a high contrast.

7 Claims, 3 Drawing Sheets

FIG. 1

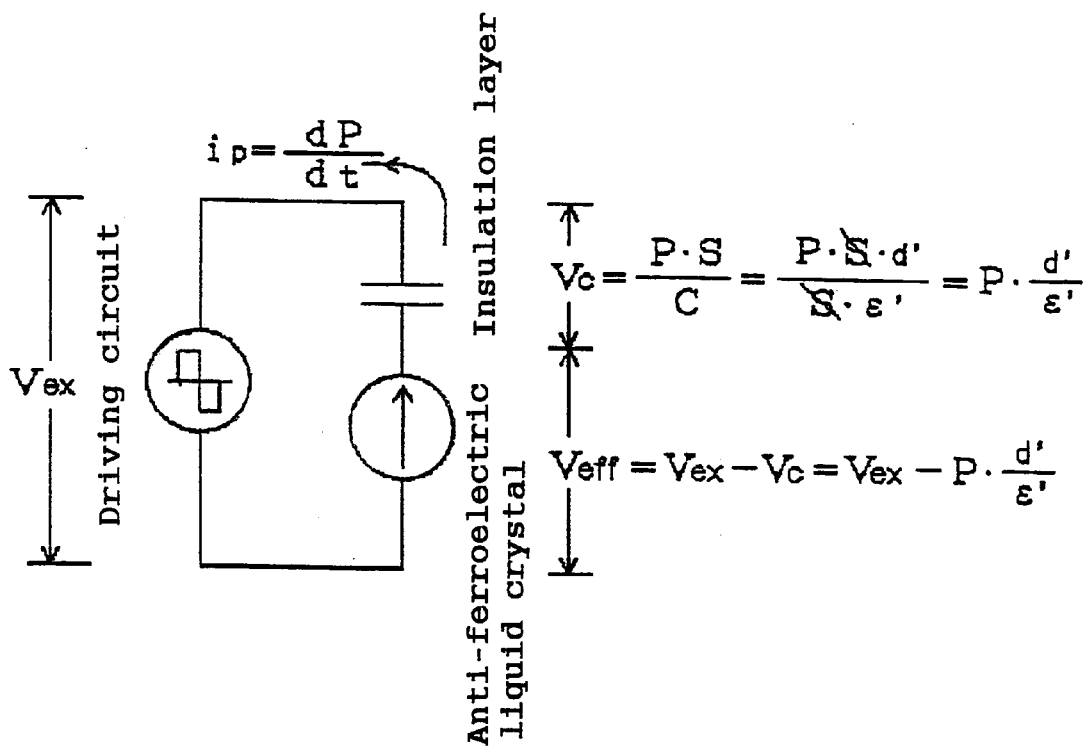

Vex: Drive voltage applied to device

Vc: Voltage generated between the upper and lower surfaces of an alignment layer by the charge of a polarization inversion current Veff: Effective voltatage actually applied to liquid crystal P: Polarization of liquid crystal ip: Polarization inversion current S: Electrode area of liquid crystal device d': Thickness of alignment layer ε': Dielectric constant of alignment layer Eeff: Electric field actually applied to liquid crystal
d: Thickness of liquid crystal layer
Ci (i = 1 ~ 4): Threshold in device having no alignment layer Alignment layer factor: $\alpha = \dfrac{d'}{\varepsilon'} \cdot \dfrac{1}{d}$ Apparent electric field strength:

$$E_{ex} = \dfrac{V_{ex}}{d} = E_{eff} + \alpha \cdot P$$

RACEMIC COMPOUND AND ANTI-FERROELECTRIC LIQUID CRYSTAL COMPOSITION CONTAINING THE COMPOUND

The present invention relates to a novel racemic compound, a novel anti-ferroelectric liquid crystal composition containing the same and a liquid crystal display device for which the composition is used.

A liquid crystal display device has been so far developed as an attractive display device due to its low-voltage operation, low-power consumption and display capability with a thin screen. Further, the liquid crystal display device is recently practically being applied to the fields of information and office automation-related machines and equipment and the field of television sets, and simultaneously, it is being applied to various fields of other use.

Under the circumstances, energetic developments are under way for attaining a large-sized liquid crystal display device of higher performance that has a higher display capacity and a higher display quality than a conventional CRT display device.

Liquid crystals used in currently available liquid crystal display devices are nematic liquid crystals, and they are classified into simple matrix driven liquid crystals and active matrix driven liquid crystals according to their driving methods.

Simple matrix driven liquid crystal display devices are produced advantageously in view of a cost due to their simple structures. However, these devices have the problems that the contrast is low due to a cross-talk phenomenon, that driving in a large capacity is difficult and that the display of video frame rate is difficult due to a slow response speed.

It is therefore necessary to break through many technical problems for attaining a large-sized liquid crystal display device capable of displaying the video frame rate.

On the other hand, while active matrix driven liquid crystal display devices use a TFT (thin film transistor) method as a main stream, it is required to form thin film transistors for each of pixels, and a large investment is required for high production technology and the construction of a production line. The active matrix driving method is therefore far disadvantageous in view of a cost as compared with the simple matrix driving method. However, the active matrix driven liquid crystal display device has a high contrast since the cross-talk phenomenon which is a problem of the simple matrix driving method is few, and further, its response speed is fast. Therefore, there can be attained a liquid crystal display device which has a high image quality and is capable of displaying the video frame rate. For this reason, the TFT method among the active matrix driving methods is gaining its position as a main stream.

At present, large-sized liquid crystal devices having a size of 10 to 20 inches are being developed in which a nematic liquid crystal is mainly used, and with the development of such devices, problems associated with viewing angle dependency which is inevitable to a device using the nematic liquid crystal become extremely critical. Various technical studies have been made for overcoming the viewing angle dependency, and as a result, displaying with a viewing angle of about 140° has become possible without the occurrence of a gray scale inversion. However, the contrast is still greatly dependent upon a viewing angle, and at present, there can not yet be obtained such flat contrast characteristics with regard to the wide viewing angle as achieved in CRT.

Under the above circumstances, a liquid crystal display device using a ferroelectric liquid crystal attracts attention as a fast response liquid crystal display device. A surface stabilized ferroelectric liquid crystal (SSFLC) device disclosed by Clark and Lagerwall attracts attention due to its fast response speed and wide viewing angle which have not been available in the past. Its switching characteristics have been studied in detail, and a number of ferroelectric liquid crystal compounds have been synthesized for optimizing various physical property constants. In accomplishing a practical device, though there have been a number of technical barriers to be overcome such as difficulties in attainment of a memory effect and control of a layer structure due to the difficulty in an alignment control, destruction of an alignment caused by a mechanical shock, and the like, these problems have been overcome to produce a device as a product.

However, the ferroelectric liquid crystal display device still has problems that it cannot have color display since a gray scale is, in principle, not possible and that the display of the video frame rate is difficult to obtain because high speed response has not been attained yet.

Further, as another fast liquid crystal display device, the development of a device having a switching mechanism different from that of SSFLC is also under way. It is a liquid crystal display device which utilizes switching among tn-stable states of a liquid crystal compound having an anti-ferroelectric phase (to be referred to as "anti-ferroelectric liquid crystal compound" hereinafter) (Japanese Journal of Applied Physics, Vol. 27, pp. L729, 1988).

An anti-ferroelectric liquid crystal device has three stable states. That is, two uniform states (Ur, Ul) and a third state observed in a ferroelectric crystal device. Chandani et al report that the above third state is an anti-ferroelectric phase (Japanese Journal of Applied Physics, vol. 28, pp. L1261 (1989) and Japanese Journal of Applied Physics, vol. 28, pp. L1265 (1989)). The above switching among the tri-stable states is the first characteristic of an anti-ferroelectric liquid crystal device.

The second characteristic of the anti-ferroelectric liquid crystal device is that a sharp threshold is present with regard to an applied voltage.

Further, it has a memory effect when a proper bias voltage is set, which is the third characteristic of the anti-ferroelectric liquid crystal device.

Further, the fourth characteristic of the anti-ferroelectric liquid crystal is that its layer structure can be easily switched when an electric field is applied (Japanese Journal of Applied Physics, Vol. 28, pp. L119, (1989), vol. 29, pp. L111 (1990)). Owing to this characteristic, a liquid crystal display device having few defects and self-restoring ability of the alignment can be produced.

By utilizing those characteristics described above, a liquid crystal device having a high response speed and an excellent contrast can be achieved.

Further, it has been demonstrated that the gray scale, which is almost impossible to achieve with a ferroelectric liquid crystal device, is possible to achieve with an anti-ferroelectric liquid crystal device. It has been consequently made possible to shift toward a full-color display, and the importance of an anti-ferroelectric liquid crystal is increasing (Preprints of No. 4 Ferroelectric Liquid Crystal International Symposium, page 77, (1993)).

Under the circumstances, energetic developments are under way for achieving an anti-ferroelectric liquid crystal display device, but the developments are presently encountering the following problems.

When an anti-ferroelectric liquid crystal is used as a display device, the anti-ferroelectric liquid crystal is generally sandwiched between two glass substrates coated with an insulation layer and an alignment layer. The insulation layer is necessary for preventing a short circuit between the substrates, and it is required to have a certain thickness for the complete prevention of a short circuit. On the other hand, the alignment layer is required for aligning liquid crystal molecules in a certain direction, and it is also required to have a certain thickness so as to reduce alignment defects, which occur when the liquid crystal molecules are aligned, as small as possible, like the case of the insulation layer.

When a voltage is applied to the thus formed liquid crystal device, the phase transition from an anti-ferroelectric state to a ferroelectric state occurs sharply with regard to the applied voltage in the case where the insulation layer and the alignment layer have a small thickness or are completely absent. However, when the insulation layer and the alignment layer have a thickness required for practical use, the phase transition from the anti-ferroelectric state to the ferroelectric state takes place moderately with regard to the applied voltage.

In the driving of an anti-ferroelectric liquid crystal, a holding voltage lower than a writing voltage is continuously applied for a predetermined period of time after the writing voltage is applied, for producing a memory effect.

When the phase transition from an anti-ferroelectric state to a ferroelectric state takes place moderately with regard to an applied voltage as described above, that is, when a liquid crystal display device has a low steepness of threshold, the holding voltage that can be selected is limited to a very narrow range, and in an extreme case, the holding voltage cannot be set, and no memory effect is secured. This means that such device can not be used as an anti-ferroelectric liquid crystal display device, which is a serious problem.

Further, the lower the steepness of threshold in the device, the narrower the breadth of the holding voltage that can be selected, and a so-called driving margin decreases accordingly. A practical device is therefore required to have a high steepness of threshold, and liquid crystal materials which can give such a steepness of threshold are therefore being demanded.

Practically, as described above, it is preferred that an anti-ferroelectric liquid crystal be a material capable of giving a high steepness of threshold when used in a liquid crystal device.

As described above, it was experimentally known that the steepness of threshold of a liquid crystal device was closely related with the thickness of each of the insulation layer and the alignment layer.

Studies have been made to determine what factors can explain the above relationship. In the following studies, both an insulation layer and an alignment layer will be together referred to as an "alignment layer".

For facilitating the understanding of the studies, the studies will be explained with reference to FIGS. 1 to 4 below.

BRIEF DESCRIPTION OF THE DRAWINGS

Brief explanation of the drawing

FIG. 1 shows an equivalent circuit of an anti-ferroelectric liquid crystal device.

Figure 2:
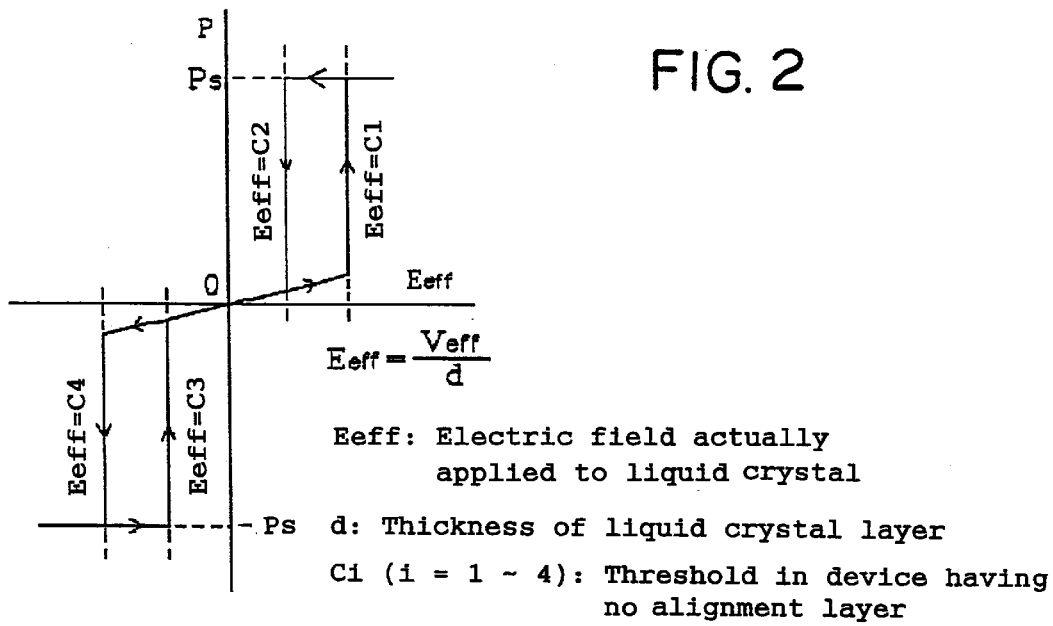

FIG. 2 shows a simulation result on the steepness of threshold when no alignment layer is present.

Figure 3:
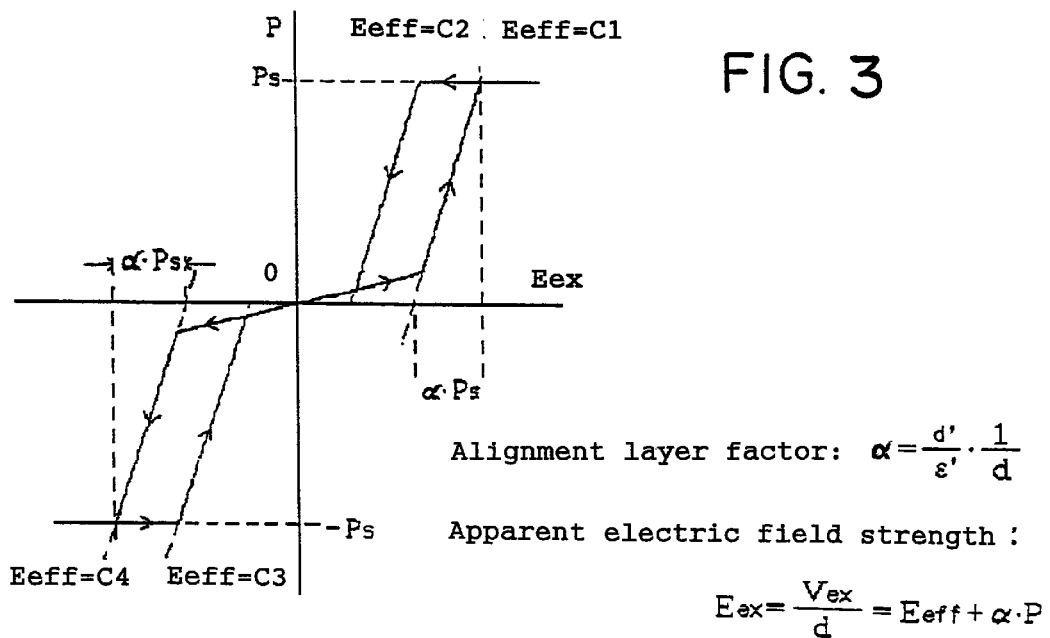

FIG. 3 shows a simulation result on the steepness of threshold when an alignment layer is present.

Figure 4:
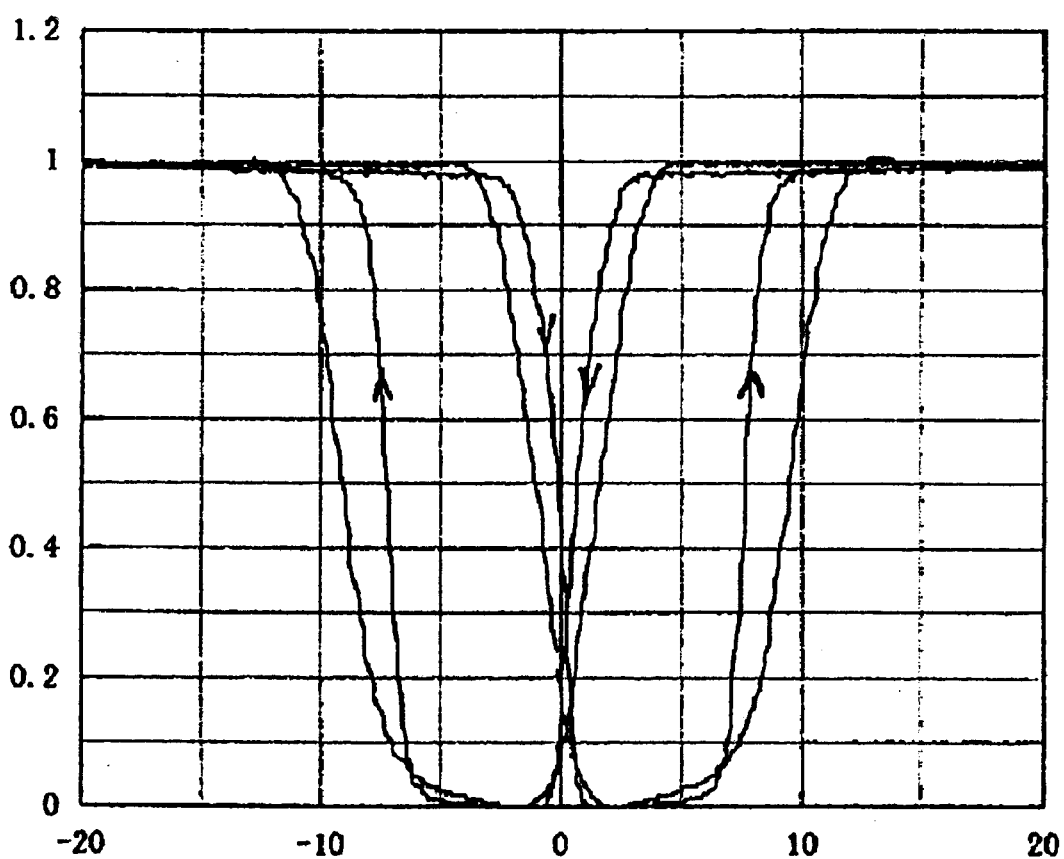

FIG. 4 shows optical responses in Comparative Example 1 and Example 9, wherein a hysteresis with arrows shows the optical response in Example 9, while a hysteresis without arrows shows the optical response in Comparative Example 1.

DETAILED DESCRIPTION OF THE INVENTION

FIG. 1 shows an equivalent circuit which comprises an electric current source to generate a polarization current according to an applied voltage, an alignment layer that is an electrostatic capacitor C to connected to an anti-ferroelectric liquid crystal in series, and a driving circuit that is an ideal voltage source.

In FIG. 1, the drive voltage applied to a device is taken as Vex, a voltage generated between the upper and lower surfaces of an alignment layer by the charge of a polarization inversion current is taken as Vc, an effective voltage to be actually applied to the liquid crystal is taken as Veff, a spontaneous polarization of the liquid crystal is taken as P, an electrode area of the liquid crystal device is taken as S, a thickness of the alignment layer is taken as d', and a dielectric constant of the alignment layer is taken as $\epsilon'$. Vc is calculated as in the following equation (1).

$$Vc = PS/C = PSd'/(S\epsilon') = P(d'/\epsilon') \quad (1)$$

On the basis of the above equation, Veff is expressed as in the following equation (2).

$$Veff = Vex - Vc = Vex - P(d'/\epsilon') \quad (2)$$

As shown in the equation (2), the voltage actually applied to the liquid crystal is lower than the externally applied voltage by a product of the polarization P of the liquid crystal, the thickness d' of the alignment layer and a reciprocal number $1/\epsilon'$ of the dielectric constant of the alignment layer.

Then, when a thickness of the liquid crystal layer filled in a liquid crystal cell is taken as d, an electric field Eeff actually applied to the liquid crystal is expressed by the following equation (3).

$$Eeff = Veff/d \quad (3)$$

On the other hand, an apparent electric field strength Eex is expressed by the following equation (4).

$$Eex = Vex/d = (Veff + Vc)/d = Veff/d + P(d'/\epsilon')/d = Eeff + \alpha \quad (4)$$

wherein $$\alpha = d'/(\epsilon' d) \quad (5)$$

When no alignment layer is present, the second term in the equation (4) is 0, and hence Eex=Eeff.

While an anti-ferroelectric liquid crystal shows a hysteresis of its optical response with regard to an applied voltage, four thresholds are thinkable with regard to the hysteresis.

Each threshold is Eeff (=Eex), and in this case, these thresholds do not incline to an electric field. FIG. 2 shows this appearance.

When an alignment layer is present, the equation (4) is modified to obtain the following equation (6).

$$Eeff = Eex - \alpha P \quad (6)$$

That is, an effective electric field exerting on the liquid crystal is lower than the applied electric field Eex by $\alpha \cdot P$. As a result, the hysteresis is strained to a great extent due to the contribution of the $\alpha \cdot P$ as shown in FIG. 3.

The above studies show that the strain of hysteresis is greatly caused by mutual effects of the spontaneous polarization and the alignment layer. Therefore, for obtaining a liquid crystal device having a reduced strain of hysteresis, it is required to decrease the above mutual effects as low as possible.

For the above purpose, the measures that can be specifically taken include the use of an alignment layer having a high dielectric constant, decreasing the thickness of the alignment layer and decreasing the spontaneous polarization of the liquid crystal, as is clear from the above equations (5) and (6).

In the above measures, since there are not many kinds of industrially usable compounds having a high dielectric constant, it is rather difficult to select an usable alignment layer. Consequently, the measures that can be specifically taken include decreasing the thickness of the alignment layer, decreasing the spontaneous polarization of the liquid crystal, and the like.

Generally, an anti-ferroelectric liquid crystal compound has a considerably large spontaneous polarization, and a liquid crystal compound having relatively excellent physical properties has a spontaneous polarization of 200 nC/cm$^2$ or more. Therefore, unless the thickness of the alignment layer is much decreased, the strain of the hysteresis becomes considerably large. However, when the thickness of the alignment layer is decreased, there occurs a problem that the alignment state of the liquid crystal molecules is too defective to secure a contrast. The measure for correcting the strain of the hysteresis by decreasing the thickness of the alignment layer is therefore considerably limited.

On the other hand, the spontaneous polarization of a liquid crystal compound can be decreased by a method in which a proper compound having no spontaneous polarization is added to the liquid crystal compound, that is, the liquid crystal compound is diluted so as to have a decreased concentration. Since the response speed of a liquid crystal is determined by a product of an applied voltage and a spontaneous polarization, however, there occurs another new problem that the response speed decreases when the spontaneous polarization is simply decreased by dilution.

Under the circumstances, in order to obtain a device having a decreased strain of hysteresis, attempts have been so far made to develop an anti-ferroelectric liquid crystal compound having a low spontaneous polarization, a low threshold voltage and a low viscosity, but it is a current situation that no satisfactory achievements have been obtained.

The present invention has been developed from the above points of view, and has been completed by finding the following. By selecting a racemic compound having a proper chemical structure and adding the compound in a specific proportion as means of decreasing the spontaneous polarization for decreasing the strain of hysteresis of an anti-ferroelectric liquid crystal compound, the spontaneous polarization can be decreased without decreasing the response speed, and when the composition is used for forming a liquid crystal device, the liquid crystal device having a decreased strain of hysteresis can be obtained.

That is, according to the present invention, there is provided a racemic compound of the following general formula

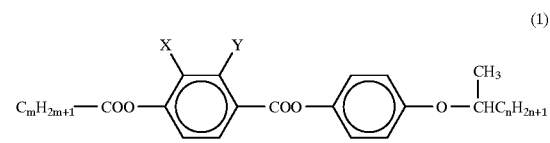

(1)

wherein m is an integer of 4 to 12, n is an integer of 4 to 10, and each of X and Y is a hydrogen atom or a fluorine atom, provided that X and Y cannot be a fluorine atom at the same time.

According to the present invention, further, there is provided an anti-ferroelectric liquid crystal composition consisting essentially of the racemic compound of the above formula (1) and an anti-ferroelectric liquid crystal compound of the following formula (2),

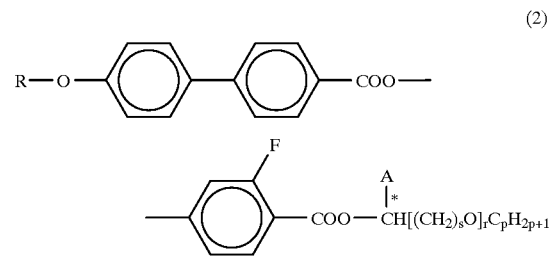

(2)

wherein R is a linear alkyl group having 6 to 12 carbon atoms, A is —CH$_3$ or —CF$_3$ and r is 0 or 1 provided that when A is —CH$_3$, r is 0 and p is an integer of 4 to 10, that when A is —CF$_3$, r is 1, s is an integer of 6 to 8 and p is an integer of 2 or 4. C* is an asymmetric carbon atom.

The present invention will be more specifically explained hereinafter.

In the above general formula (1) of the racemic compound of the present invention, m is an integer of 4 to 12, preferably 6 to 10, and n is an integer of 4 to 10, preferably 5 to 8. Further, each of X and Y is a hydrogen atom or a fluorine atom, provided that X and Y cannot be a fluorine atom at the same time.

The racemic compound of the above general formula (1) can be easily produced by the following method.

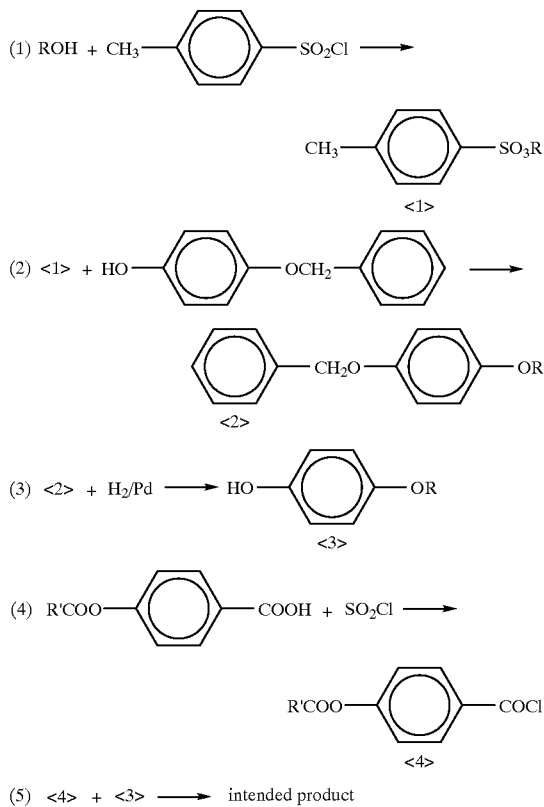

The above production method will be briefly explained below.

(1) shows a reaction between p-toluene sulfonyl chloride and racemic 2-alkanol.
(2) shows a reaction between a racemic 2-alkanol p-toluene sulfonic acid ester and hydroquinone monobenzylether
(3) shows the debenzylation by hydrogenation of monobenzylether obtained in (2).
(4) shows the chlorination of alkanoyl benzoic acid.
(5) shows the formation of an intended product by a reaction between <3> and <4>.

The anti-ferroelectric liquid crystal composition of the present invention consists essentially of the racemic compound of the above general formula (1) and the anti-ferroelectric liquid crystal compound of the above general formula (2).

In the above general formula (2), R is a linear alkyl group having 6 to 12 carbon atoms, preferably 8 to 10 carbon atoms, A is —$CH_3$ or —$CF_3$, provided that when A is —$CH_3$, r is 0 and p is an integer of 4 to 10, and that when A is —$CF_3$, r is 1, s is an integer of 6 to 8 and p is an integer of 2 or 4, and C* is an asymmetric carbon atom. A compound of the formula (2) in which A is —$CH_3$, r is 0 and p is an integer of 4 to 6 is particularly preferred since the compound is well-balanced in various physical properties.

The anti-ferroelectric liquid crystal compound of the general formula (2) of the present invention can be easily produced by the following method. For example, a compound of the general formula (2) in which A=$CF_3$, p=2, r=1 and s=5 is produced by the following method.

(a) AcO—Ph(Z)—COOH+$SOCl_2$→AcO—Ph(Z)—COCl
(b) (a)+HOC*H($CF_3$)($CH_2$)$_5$O$C_2H_5$→AcO—Ph(Z)—COOC*H($CF_3$)($CH_2$)$_5$O$C_2H_5$
(c) (b)+Ph—$CH_2NH_2$→HO—Ph(Z)—COOC*H($CF_3$)($CH_2$)$_5$O$C_2H_5$
(d) RO—Ph—Ph—COOH+$SOCl_2$→RO—Ph—Ph—COCl
(e) (b)+(d)→anti-ferroelectric liquid crystal compound In the above formulae, AcO— is an acetyl group, —Ph(Z)— is a 1,4-phenylene group in which fluorine may be substituted, Ph— is a phenyl group, —Ph— is a 1,4-phenylene group, and C* is an asymmetric carbon atom.

The above production method will be briefly explained below.

(a) shows the chlorination of fluorine-substituted or non-substituted p-acetoxybenzoic acid with thionyl chloride.
(b) shows a reaction between a chlorination product obtained in (a) and an alcohol to form an ester.
(c) shows the deacetylation of the ester obtained in (b).
(d) shows the chlorination of alkyloxybiphenyl carboxylic acid.
(e) shows the formation of a liquid crystal by a reaction between a phenol obtained in (c) and a chlorination product obtained in (d).

The anti-ferroelectric liquid crystal composition of the present invention consists essentially of the racemic compound of the above general formula (1) and the anti-ferroelectric liquid crystal compound of the formula (2). Specifically, it is advantageous that the total amount of the compounds of the formulae (1) and (2) based on the total composition is at least 70 mol %, preferably at least 80 mol %.

The mixing ratio ((1):(2)) of the compound of the above general formula (1) to the compound of the above general formula (2) is preferably in the range of 1:99 to 40:60, particularly preferably 5:95 to 35:65, in terms of a molar ratio.

Further, the compound of the above general formula (2) may be used singly or as a mixture of at least two compounds. A liquid crystal display device that is excellent in alignment characteristics and steepness of threshold and exhibits a high contrast can be obtained in some cases where a mixture of at least two compounds of the formula (2) is used.

It is preferred from the practical stand point that the anti-ferroelectric liquid crystal composition of the present invention have at least a smectic A phase, and that an upper-limit temperature of the temperature range of anti-ferroelectric phase thereof be 40° C. or higher and a lower-limit temperature thereof be 0° C. or lower. The anti-ferroelectric liquid crystal composition of the present invention is preferably used in an anti-ferroelectric liquid crystal display device formed by interposing the composition between a pair of electrode substrates.

The present invention can provide a novel racemic compound and a novel anti-ferroelectric liquid crystal composition. Furthermore, the novel anti-ferroelectric liquid crystal composition of the present invention can provide an anti-ferroelectric liquid crystal display device which is excellent in steepness of threshold, has an anti-ferroelectric phase over a broad temperature range, exhibits a high response speed and therefore has a high display quality and a high contrast.

EXAMPLES

The present invention will be explained with reference to Examples and Comparative Examples hereinafter, while the present invention shall not be limited thereto.

EXAMPLE 1

Preparation of 4-(1-methylheptyloxy)phenyl=4'-decanonyloxy benzoate (E1) (formula (1): m=9, n=6, X=H, Y=H):

(1) Preparation of p-toluene sulfonic acid (1-methyl) heptyl 3.5 Grams of 2-octanol and 15 ml (milliliter) of pyridine were put in a reaction vessel and the mixture was cooled to −20° C. 6.3 Grams of p-toluene sulfonyl chloride was added, under stirring, thereto at one time, then the mixture was continued to be stirred at the same temperature for 30 minutes and thereafter, at a room temperature for another 4 hours.

The reaction mixture was poured into ice water and extracted with dichloromethane.

An organic phase was washed with water and dried over anhydrous sodium sulfate. The solvent was distilled off to give 5.9 g (yield 74%) of an intended product.

(2) Preparation of 4-benzyloxyphenyl-1-methylheptylether 5.9 Grams of p-toluene sulfonic acid (1-methyl) heptyl obtained in (1), 4.5 g of hydroquinone mono benzyl ether, 2.4 g of potassium hydroxide and 28 ml of ethanol were put in a reaction vessel and the mixture was stirred at a room temperature for 2 hours. The mixture was further refluxed under heating for 1 hour.

The reaction mixture was poured into water and extracted with dichloromethane, and an organic phase was consecutively washed with 1N hydrochloric acid and with water, and an organic layer was dried over anhydrous sodium sulfate. Then, the solvent was distilled off to give a crude product.

Silica gel column chromatography (effluent: hexane/ethyl acetate=925/75) was used for purification of the crude product to give 150 g (yield 67%) of an intended product.

(3) Production of 4-(1-methylheptyloxy)phenol 0.2 Grams of a 10% palladium carbon catalyst was put in a reaction vessel and the inside of the system was substituted with a nitrogen gas. Then, 4.5 g of 4-benzyloxyphenyl-1-methylheptylether and 30 ml of ethanol were added thereto and the inside of the system was substituted with hydrogen. The reaction was carried out for 8 hours with hydrogen being supplied to the vessel through a gas burette.

After the inside of the system was substituted with nitrogen, the catalyst was filtered out and the solvent was distilled off to give 3 g (yield 97%) of an intended product.

(4) Production of 4-(1-methylheptyloxy)phenyl=4'-decanoyloxyphenylbenzoate 1.0 Gram of 4-decanoyloxy benzoic acid and 20 ml of thionyl chloride were added to a reaction vessel and the mixture was further ref luxed under heating for 4 hours. Then, excessive thionyl chloride was distilled off under reduced pressure, and then 20 ml of dichloromethane and 0.5 g of 4-(1-methylheptyloxy)phenol obtained in the above (3) were added to the resultant benzoic acid chloride. The mixture was stirred for 5 hours, and was consecutively washed with hydrochloric acid, with sodium hydroxide aqueous solution and with water. The solvent was distilled off, and silica gel chromatography (effluent: hexane/ethyl acetate=94/6) was used for purification of the obtained crude product to give 0.65 g (yield 60%) of an intended product.

Table 1 shows NMR spectral data of the resultant intended product.

Examples 2 to 8

The compounds in the following Examples 2 to 8 (E2 to E8) were produced under the same reaction conditions as in Example 1.

Table 1 shows NMR spectral data of each compound.

Example 2; (formula (1): m=6, n=6, X=H, Y=H) 4-(1-methylheptyloxy)phenyl=4'-heptanoyloxyphenyl-benzoate (E2)

Example 3; (formula (1): m=8, n=6, X=H, Y=H) 4-(1-methylheptyloxy)phenyl=4'-nonanoyloxyphenylbenzoate (E3)

Example 4; (formula (1): m=10, n=6, X=H, Y=H) 4-(1-methylheptyloxy)phenyl=4'-undecanoyloxyphenyl-benzoate (E4)

Example 5; (formula (1): m=9, n=5, X=H, Y=H) 4-(1-methylhexyloxy)phenyl=4'-decanoyloxyphenylbenzoate (E5)

Example 6; (formula (1): m=9, n=8, X=H, Y=H) 4-(1-methylnonyloxy)phenyl=4'-decanoyloxyphenylbenzoate (E6)

Example 7; (formula (1): m=9, n=6, X=F, Y=H) 4-(1-methylheptyloxy)phenyl=3'-fluoro-4'-decanoyloxyphenyl benzoate (E7)

Example 8; (formula (1): m=9, n=6, X=H, Y=F) 4-(1-methylheptyloxy)phenyl=2'-fluoro-4'-decanoyloxyphenyl benzoate (E8)

Comparative Example 1

The following anti-ferroelectric liquid crystal compounds 1A and 1B were mixed in a mixing ratio of 70/30 (molar ratio) to obtain an anti-ferroelectric liquid crystal composition.

1A: $C_9H_{19}$—O—Ph—Ph—COO—Ph(3F)—COO—$C^*H$($CF_3$)($CH_2$)$_5OC_2H_5$

1B: $C_8H_{17}$—O—Ph—Ph—COO—Ph(3F)—COO—$C^*H$($CH_3$)$C_5H_{11}$

In the above formulae, —Ph— is a 1,4-phenylene group, —Ph(3F)— is a 1,4-phenylene group containing fluorine substituted on the 3-position, and $C^*$ is an asymmetric carbon atom.

The phase sequence of the resultant composition was identified by texture observation and DSC measurement. Table 2 shows the results. Then, the liquid crystal composition was measured for a spontaneous polarization at 40° C. and a response time in the transition from an anti-ferroelectric state to a ferroelectric state. Table 2 shows the results.

Shown in FIG. 4 is an optical response hysteresis with regard to an applied voltage when a triangular wave voltage was applied to the anti-ferroelectric liquid crystal compositions at 40° C. (indicated without arrows). A large strain of hysteresis was observed.

The optical response hysteresis, response time and spontaneous polarization were measured as follows.

A liquid crystal cell (cell thickness 2 μm) having ITO electrodes and a rubbed polyimide thin film (30 nm) was charged with a liquid crystal composition in an isotropic state. Then, the cell was gradually cooled at a rate of 1.0° C./minute to align the liquid crystal.

The cell was interposed between the crossed polarizers such that the layer direction of the liquid crystal was in parallel with an analyzer or a polarizer, and then the liquid crystal composition was measured for an optical response hysteresis with a photo-multiplier.

The response time in a transition from an anti-ferroelectric state to a ferroelectric state was defined to be an amount of time required for a change in transmittance from 10% to 90% with a maximum transmittance defined to be 100% and a minimum transmittance to be 0%, under the application of 25 V having a frequency of 10 Hz at 40° C.

The spontaneous polarization was determined by applying a 25 V triangular wave at 40° C. and measuring a polarization inversion current.

Example 9

49 Mol % of the anti-ferroelectric liquid crystal compound 1A and 21 mol % of the anti-ferroelectric liquid crystal compound 1B used in Comparative Example 1 and 30 mol % of the racemic compound (E2) obtained in Example 1 were mixed to give an anti-ferroelectric liquid crystal composition. Table 2 shows the phase sequence, spontaneous polarization and response time of the resultant composition. FIG. 4 shows an optical response hysteresis (indicated with arrows).

As is clear from Table 2, while the response time was almost the same as that in Comparative Example 1, the spontaneous polarization was largely decreased. Further, as obvious from the comparison of the hysteresis with arrows and the one without arrows in FIG. 4, a hysteresis characteristic was improved.

TABLE 1

| Example No. (Abbreviated) | Chemical shift (ppm) | | | | | | | | |
|---|---|---|---|---|---|---|---|---|---|
| | 1H | 2H | 3H | 4H | 5H | 6H | 7H | 8H | 9H |
| 1~6 (E1~E6) | 2.6 | 6.9 | 7.2 | 7.2 | 8.2 | 1.6 | 4.3 | 1.6 | |
| 7 (E7) | 2.6 | 7.2 | 8.0 | 8.0 | 6.9 | 7.1 | 1.4 | 4.4 | 1.4 |
| 8 (E8) | 2.6 | 8.1 | 7.0 | 7.0 | 6.9 | 7.1 | 1.4 | 4.3 | 1.4 |

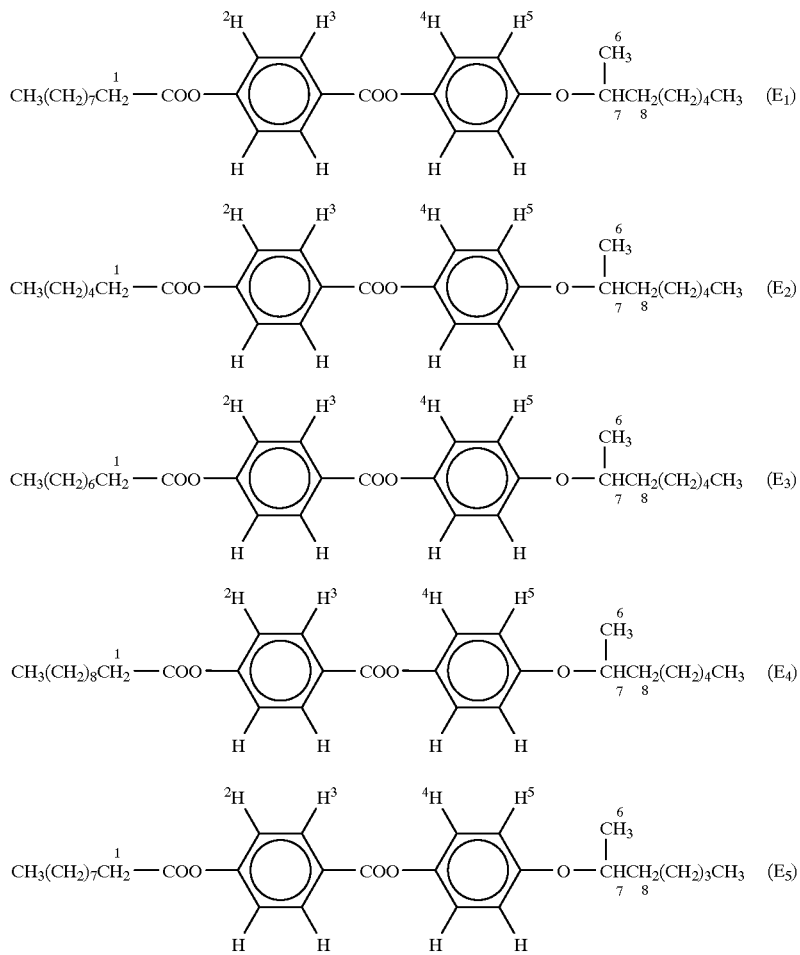

-continued

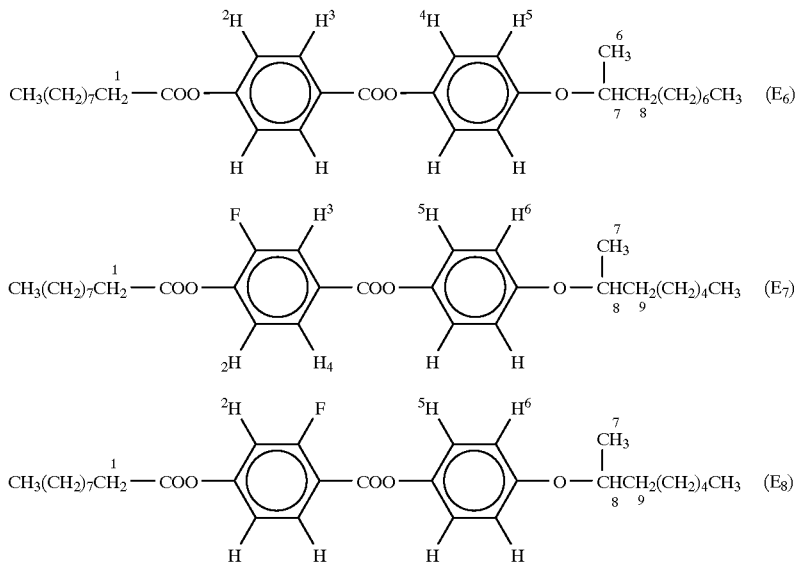

TABLE 2

| | Phase sequence | Spontaneous polarization (nC/cm$^2$) | Response time (μ sec.) |
|---|---|---|---|
| Comparative Example 1 | Cr(<-20)SCA*(95)SC*(87)SA(105)I | 193 | 86 |
| Example 9 | Cr(<-20)SCA*(61)SC*(67)SA(88)I | 96 | 86 |

Parenthesized values in Phase sequence show temperatures (° C.).
Abbreviations stand for the following.
Cr: crystal phase
SCA*: anti-ferroelectric phase
SC*: ferroelectric phase
SA: smectic A phase
I: isotropic phase Measured temperature of the spontaneous polarization and the response time was 40° C.

What is claimed is:

1. An anti-ferroelectric liquid crystal composition, consisting essentially of the racemic compound of the following general formula (1)

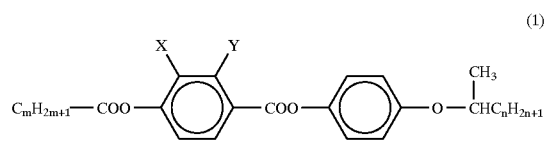

(1)

wherein m is an integer of 4 to 12, n is an integer of 4 to 10 and each of X and Y is a hydrogen atom or a fluorine atom, provided that X and Y cannot be a fluorine atom at the same time, and an anti-ferroelectric liquid crystal compound of the following general formula (2)

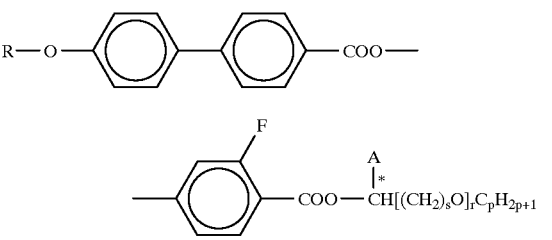

(2)

wherein R is a linear alkyl group having 6 to 12 carbon atoms, A is —CH$_3$ or —CF$_3$ and r is 0 or 1 provided that when A is —CH$_3$, r is 0 and p is an integer of 4 to 10, that when A is —CF$_3$, r is 1, s is an integer of 6 to 8 and p is an integer of 2 or 4, and C* is an asymmetric carbon atom.

2. The anti-ferroelectric liquid crystal composition of claim 1, wherein the composition has the general formula (1) in which m is an integer of 6 to 10 and n is an integer of 5 to 8.

3. The anti-ferroelectric liquid crystal composition of claim 1, wherein the composition has the general formula (2) in which A is —CH$_3$, r is 0 and p is an integer of 4 to 6.

4. The anti-ferroelectric liquid crystal composition of claim 1, wherein the composition contains the racemic compound of the general formula (1) and the anti-ferroelectric liquid crystal compound of the general formula (2) in a proportion of from 1:99 to 40:60 in terms of a molar ratio.

5. The anti-ferroelectric liquid crystal composition of claim 1, wherein at least a smectic A phase is present on a higher temperature side than an anti-ferroelectric phase and the anti-ferroelectric phase has an upper-limit temperature of 40° C. or higher and a lower-limit temperature of 0° C. or lower.

6. The anti-ferroelectric liquid crystal composition of claim 1, wherein at least 2 compounds selected from the anti-ferroelectric liquid crystal compounds of the general formula (2) are used as a mixture.

7. An anti-ferroelectric liquid crystal display device formed by interposing the anti-ferroelectric liquid crystal composition of claim 1 between a pair of electrode substrates.

* * * * *